United States Patent [19]

Cross et al.

[11] 4,230,714

[45] Oct. 28, 1980

[54] IMIDAZOLE THERAPEUTIC AGENTS

[75] Inventors: Peter E. Cross, Canterbury; Roger P. Dickinson, Dover, both of England

[73] Assignee: Pfizer Inc., New York, N.Y.

[21] Appl. No.: 61,807

[22] Filed: Jul. 30, 1979

[30] Foreign Application Priority Data

Aug. 15, 1978 [GB] United Kingdom ............... 33456/78

[51] Int. Cl.$^2$ .................... A61K 31/44; C07D 401/06; A61K 31/47
[52] U.S. Cl. ................................... 424/263; 424/258; 546/176; 546/278
[58] Field of Search ................ 546/176, 278; 424/258, 424/263

[56] References Cited

U.S. PATENT DOCUMENTS

| 3,417,091 | 12/1968 | Pickholz et al. ..................... 546/176 |
| 4,058,614 | 11/1977 | Baldwin ............................. 546/278 |

FOREIGN PATENT DOCUMENTS 827870 10/1975 Belgium .................................. 548/176

OTHER PUBLICATIONS

Sundberg "J. Het. Chem.", vol. 14, pp. 1279–1281, 1977.

*Primary Examiner*—Henry R. Jiles
*Assistant Examiner*—Robert T. Bond
*Attorney, Agent, or Firm*—Connolly and Hutz

[57] ABSTRACT

A series of 2-(imidazol-1-ylmethyl)pyridines and 2-(imidazol-1-ylmethyl)quinolines has been prepared, including their pharmaceutically acceptable acid addition salts. These particular compounds are useful in therapy for the treatment of ischaemic heart disease, migraine, transient ischaemic attack and stroke. Preferred member compounds include 2-(imidazol-1-ylmethyl)-3-methoxypyridine, 2-(imidazol-1-ylmethyl)-3-methoxy-6-methylpyridine and 2-(imidazol-1-ylmethyl)-3-benzyloxypyridine, respectively. Alternate methods of preparation are provided and the principal synthetic routes leading to the preferred compounds are described in some detail.

14 Claims, No Drawings

IMIDAZOLE THERAPEUTIC AGENTS

BACKGROUND OF THE INVENTION

This invention relates to certain imidazole derivatives, specifically, to certain 2-(imidazol-1-ylmethyl)-pyridines and the corresponding quinolines. These particular compounds are able to selectively inhibit the action of the thromboxane synthetase enzyme without significantly inhibiting the action of the prostacyclin synthetase or cyclooxygenase enzymes. The compounds of the invention therefore are useful, for example, in the treatment of ischaemic heart disease, stroke, transient ischaemic attack and migraine.

SUMMARY OF THE INVENTION

The compounds of the invention are organic bases of the formula:

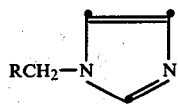
(I)

wherein R is 2-quinolyl or a pyridyl moiety of the formula:

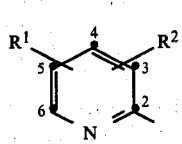
1 wherein $R^1$ is hydrogen, halogen or alkyl of 1–4 carbon atoms; and $R^2$ is alkyl of 1–4 carbon atoms, or a group of the formula —$OR^3$ wherein $R^3$ is hydrogen, alkyl of 1–4 carbon atoms, allyl, prop-2-ynyl, cycloalkylmethyl wherein the cycloalkyl group has 3–6 carbon atoms, or benzyl in which the phenyl moiety is unsubstituted on the ring or is monosubstituted with halogen, alkyl of 1–4 carbon atoms or alkoxy of 1–4 carbon atoms, with the proviso that said —$OR^3$ is always a group located at the 3- or 5- positions of the pyridine ring; and the pharmaceutically acceptable acid addition salts thereof.

The compound in which $R^1$ and $R^2$ are both hydrogen is disclosed by R. J. Sundberg et al., in the *Journal of Heterocyclic Chemistry*, Vol. 14, p. 1279 (1977), but merely as a potential transition metal ligand.

The preferred compounds of the invention are 2-(imidazol-1-ylmethyl)-3-methoxypyridine, 2-(imidazol-1-ylmethyl)-3-methoxy-6-methylpyridine and 2-(imidazol-1-ylmethyl)-3-benzyloxypyridine, respectively.

In addition, the invention provides a pharmaceutical composition comprising a compound of the formula (I), or a pharmaceutically acceptable acid addition salt thereof, together with a pharmaceutically acceptable carrier or diluent. The pharmaceutical composition is preferably in unit dosage form (as hereinafter defined).

By the term "unit dosage form" as used herein is meant a physically discrete unit containing an individual quantity of the active component in association with a pharmaceutically acceptable carrier or diluent, the quantity of active component being such that at least one unit or severable fraction of a unit is required for a single therapeutic administration. In the case of severable units, such as scored tablets, at least one severable fraction such as a one-half or one-quarter of the unit may be all that is required for a single therapeutic administration. It will be appreciated that the term "unit dosage form" does not include mere solutions except when the solutions are packaged in ingestible containers, e.g. soft capsules, or have been prepared so as to be suitable for parenteral administration, e.g., in vials of solution suitable for parenteral injection.

The invention also provides a method of inhibiting the action of the thromboxane synthetase enzyme in an animal, including a human being, without significantly inhibiting the action of the prostacyclin synthetase or cyclo-oxygenase enzymes, which comprises administering to the animal an effective amount of a compound of the formula (I), or a pharmaceutically acceptable acid addition salt thereof, or a pharmaceutical composition comprising such a compound or salt together with a pharmaceutically acceptable carrier or diluent.

Pharmaceutically acceptable acid addition salts of the compounds of the invention are salts with acids containing pharmaceutically acceptable anions, e.g., the hydrochloride, hydrobromide, sulfate or bisulfate, phosphate or acid phosphate, acetate, maleate, fumarate, lactate, tartrate, citrate, gluconate, succinate and p-toluenesulfonate salts.

In this specification, the term "halogen" means fluorine, iodine, chlorine or bromine, while alkyl in the definition of $R^1$, $R^2$ and $R^3$ simply refers to a straight or branched chain. Preferred alkyl groups have from one to two carbon atoms. The preferred cycloalkyl group is cyclopropyl.

DETAILED DESCRIPTION OF THE INVENTION

The compounds of the invention may be prepared by a number of routes, including the following:

(1) The compounds of the invention, other than the pyridines in which $R^2$ is hydroxy, can be prepared by the following reaction scheme:

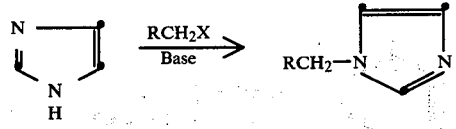

wherein X is a facile leaving group such as chlorine or bromine. In a typical procedure, the reactants are heated together, e.g., on a steam bath, in a suitable solvent, such as N,N-dimethylformamide or dimethylsulfoxide, and in the presence of a suitable base, e.g., sodium or potassium carbonate, for a period of up to 24 hours. The reaction mixture is then evaporated to dryness and the residue taken up in a suitable solvent, e.g., chloroform. The resulting mixture is then filtered and evaporated, which may leave the product as a solid which can be recrystallized from a suitable solvent, or as an oil which may be chromatographed on, for example, silica gel, the column thereafter being eluted with a solvent system like chloroform/methanol (9:1) and the appropriate fractions are then collected. The fractions thus obtained may, for example, be combined, evaporated to an oil, the oil dissolved in diethyl ether and ethereal hydrogen chloride added to the solution in order to precipitate a hydrochloride acid addition salt therefrom. The starting materials of the formula $RCH_2X$ are either known compounds or else they may be prepared by procedures analogous to those of the prior art.

(2) When R² is 3-hydroxy, the pyridines can be prepared by the following scheme:

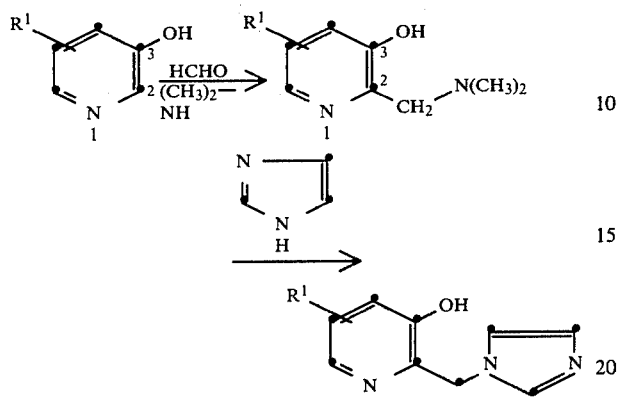

In a typical procedure, the pyridine starting material is first heated on a steam bath for a few hours in the presence of aqueous dimethylamine and formalin. The cooled solution is then extracted with ether, the combined ethereal extracts are dried and evaporated to an oil which may be distilled to give the desired 2-dimethylaminomethyl-3-hydroxy intermediate. Some of these intermediates are, in fact, known compounds. The 2-dimethylaminomethyl-3-hydroxy intermediate is then further heated in a suitable solvent, e.g., xylene, with imidazole, typically for a period of 4–8 hours. After cooling, the resulting precipitated solid is removed from the mixture by means of filtration, or when an oil precipitates it may be scratched to induce crystallization. The recovered solid is then recrystallized from a suitable solvent, e.g., isopropanol/petroleum ether.

(3) When R² is 5-hydroxy, the pyridines can be prepared by the following schemes:

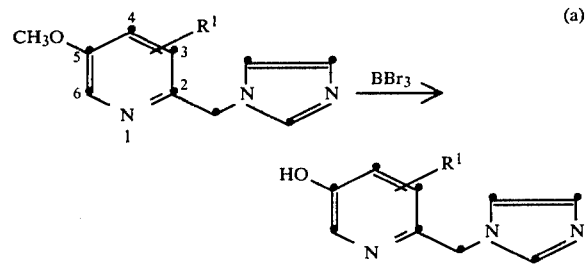

The reaction with boron tribromide is carried out according to conventional procedures (see e.g., J. F. W. McOmie et. al., Tetrahedron, 1968, 24, 2289). The 5-methoxypyridine starting materials may be prepared via route (1) as previously described.

(b) To obtain final products in which R¹ is a substituent located at the 6-position of the pyridine ring, the following reaction scheme is highly feasible:

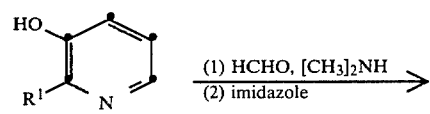

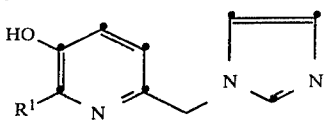

This particular reaction is carried out in a manner similar to that described in route (2) above.

(4) When R² is —OR³ and —OR³ is other than hydroxy, the corresponding pyridine compounds can be prepared by the following reaction scheme (with the —OH group in the starting material being limited to the 3- or 5-position of the molecule):

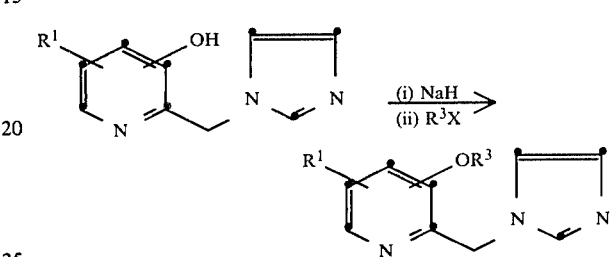

wherein X is a facile leaving group such as chlorine, bromine, methylsulfonyloxy or p-toluenesulfonyloxy, etc. In a typical procedure, the hydroxy starting material in a suitable solvent, e.g., N,N-dimethylformamide, is reacted with sodium hydride (50% suspension in mineral oil) under a dry nitrogen atmosphere for a period of up to about one hour. The compound of the formula R³X is then added dropwise, and the reesulting mixture stirred for a few hours. Water is then added and the aqueous mixture is next evaporated, with the residue subsequently being taken up in a solvent such as chloroform, filtered and then evaporated to near dryness, and the resulting mixture thereafter chromatographed on a silica gel column. The column may then be eluted first with petroleum ether to remove the mineral oil and then with chloroform. The chloroform eluant is finally evaporated and cooled, and the residue so obtained is subsequently recrystallized from a suitable solvent.

(5) The pharmaceutically acceptable acid addition salts of the compounds of the invention can be prepared by conventional procedures, e.g., by reacting a solution of the free base in a suitable solvent, e.g., diethyl ether, with a solution of the appropriate mineral or organic acid in a suitable solvent such as diethyl ether, thereby generating precipitation of the desired acid addition salt, which can subsequently be recovered from the mixture by means of filtration.

The compounds of the invention of formula (I) have been found to selectively inhibit the action of the thromboxane synthetase enzyme without significantly affecting the action of the prostacyclin synthetase or cyclooxygenase enzymes. Thus, the compounds are of value in the treatment of a wide variety of clinical conditions which are characterized by an imbalance of prostacyclin/thromboxane A₂, including migraine headache, stroke, ischaemic heart disease, thrombosis and transient ischaemic attack, as hereinafter explained below.

For instance, research work has established that in most tissues the major product of the arachidonic acid metabolism is either of two unstable substances, viz., thromboxane A₂ (TxA₂) or prostacyclin (PGI₂) (Proc. Nat. Acad. Sci. U.S.A., 1975, 72, 2994; Nature, 1976, 263, 663; Prostaglandins, 1976, 12, 897). In most cases, the prostaglandins $PGE_2$, $PGF_2$ and $PGD_2$ are comparatively minor by-products in this particular bio-synthetic pathway. The discovery of thromboxane $A_2$ and prostacyclin has significantly increased our understanding of vascular homeostasis. Prostacyclin, for example, is a powerful vasodilator and ihnibitor of platelet aggregation, and in this last respect, it is the most potent endogenous substance so far discovered. The prostacyclin synthetase enzyme is located in the endothelial layer of the vasculature and is fed by endoperoxides released by blood platelets coming into contact with the vessel wall. The prostacyclin thus produced is important for prevention of platelet deposition on vessel walls (Prostaglandins, 1976, 12, 685; Science, 1976, 17; Nature, 1978, 273, 765).

Thromboxane $A_2$, on the other hand, is synthesized by the thromboxane synthetase enzyme which is located in, for example, the blood platelets. Thromboxane $A_2$ is a powerful vasoconstrictor and pro-aggregatory substance. As such, its actions are in direct opposition to those of prostacyclin. If, for any reason, prostacyclin formation by the vasculature is impaired, then the endoperoxides produced by platelets coming into contact with the vessel wall are converted into thromboxane, but are not converted effectively into prostacyclin (Lancet, 1977, 18; Prostaglandins, 1978, 13, 3). Alteration of the prostacyclin/thromboxane balance in favor of the latter substance could result in platelet aggregation, vasospasm (Lancet, 1977, 479; Science, 1976, 1135; Amer. J. Cardiology, 1978, 41, 787) and an increased susceptibility to atherothrombosis (Lancet, (i), 1977, 1216).

It is also known that in experimental atherosclerosis, prostacyclin generation is suppressed and thromboxane $A_2$ production is enhanced (Prostaglandins, 1977, 14, 1025 and 1035). Thus, thromboxane $A_2$ has been implicated as the causative agent in variant angina, myocardial infarction, sudden cardiac death and stroke (Thromb. Haemostasis, 1977, 38, 132). Studies in rabbits have shown that electrocardiogram (ECG) changes typical of these conditions were produced when freshly prepared thromboxane $A_2$ was injected directly into the animal's heart (N. Kharasch and J. Fried (Editors), "Biochemical Aspects of Prostaglandins and Thromboxanes", Academic Press, Inc., New York, 1977, p. 189). This technique is considered to represent a unique animal model of the heart attacks of coronary patients and has been used to show that administration of a compound believed to antagonize the effects of thromboxane $A_2$ protects the rabbits from the adverse consequences of thromboxane $A_2$ injection.

Another area where a $PGI_2/TxA_2$ imbalance is considered to be a contributory factor is that of migraine. The migraine headache is associated with changes in intra- and extra-cerebral blood flow and in particular, it involves a pre-headache reduction of cerebral blood flow followed by dilation in both vascular areas during the headache phase. Prior to the development of the headache, blood levels of 5-hydroxytryptamine are elevated and this suggests the occurrence of in vivo aggregation and release of the amine from the platelet stores. It is known that the blood platelets of migraine patients are more prone to aggregate than are those of normal individuals (J. Clin. Pathol., 1971, 24, 250; J. Headache, 1977, 17, 101). Furthermore, it has now been postulated that not only an abnormality of platelet function a major factor in the pathogenesis of migraine attacks, but it is also, in fact, their prime cause (Lancet, (i), 1978, 501). Thus, a drug that selectively modifies platelet function to inhibit thromboxane $A_2$ formation would have to be of considerable benefit in migraine therapy.

Abnormalities of platelet behaviour have been reported in patients with diabetes mellitus (Metabolism, 1979, 28, 394; Lancet, 1978 (i) 235). Diabetic patients are known to be particularly susceptible to microvascular complications, atherosclerosis and thrombosis and platelet hyper-reactivity has been suggested as the cause of such angiopathy. Diabetic platelets produce elevated amounts of $TxB_2$ and malondialdehyde (Symposium "Diabetes and Thrombosis—Implications for Therapy", Leeds, U.K., April 1979). Also, it has been shown that in rats with experimental diabetes vascular prostacyclin production is impaired and $TxA_2$ synthesis from the platelets is elevated (IV International Prostaglandin Conference, Washington, D.C. May, 1979). Thus the imbalance between prostacyclin and $TxA_2$ is considered to be responsible for the microvascular complications of diabetes. A $TxA_2$-synthetase inhibitor could therefore find clinical utility in preventing these vascular complications.

Aspirin and most other non-steroidal anti-inflammatory (NSAI) drugs inhibit the cyclo-oxygenase enzyme. The effect of this action is to shut down the production of the $PGG_2/H_2$ endoperoxides and by so doing, to reduce both the prostacyclin and thromboxane $A_2$ levels. Aspirin and aspirin-like drugs have been evaluated clinically for the prevention of stroke and heart attack (New England J. Med., 1978, 299, 53; Brit. Med. J., 1978, 1188; Stroke, 1977, 8, 301). Although some encouraging results have been obtained with these drugs, a compound which specifically inhibits thromboxane $A_2$ formation while leaving the biosynthesis of prostaycylin unimpaired would, of course, necessarily be more valuable in these same clinical conditions (Lancet, (ii), 1978, 780).

The effect of the compounds of the formula (I) on the thromboxane synthetase enzyme, and the prostacyclin synthetase and cyclo-oxygenase enzymes has been measured by the following in vitro enzyme assay tests:

1. Cyclo-oxygenase

Ram seminal vesicle microsomes (Biochemistry, 1971, 10, 2372) are incubated with arachidonic acid (100 $\mu M$) at 22° C. for a period of one minute so as to produce $PGH_2$, and aliquots of this reaction mixture injected into a stream of Krebs-bicarbonate at 37° C. [containing a mixture of antagonists (Nature, 1978, 218, 1135) and indomethacin (Brit. J. Pharmacol., 1972, 45, 451)] which is superfusing a spirally-cut rabbit aorta strip (Nature, 1969, 223, 29). The ability of a compound to inhibit the enzyme is measured by comparing the increases in isometric tension produced by $PGH_2$ in the absence of the test compound and again, following pre-incubation of the enzyme with the test compound for a period of five minutes.

2. Prostacyclin ($PGI_2$) Synthetase

Pig aorta microsomes (Nature, 1976, 263, 663) are incubated with $PGH_2$ (produced as in assay test No. 1) at 22° C. for a period of 30 seconds and aliquots are then bio-assayed in the same manner as hereinbefore described. $PGI_2$ production is assessed indirectly by measuring the decrease in $PGH_2$-induced tension ($PGI_2$ itself does not contract the aorta). This decrease in tension can be prevented completely by pre-incubation of the enzyme with the selective PGI$_2$ synthetase inhibitor, known chemically as 15-hydroperoxy-arachidonic acid (Prostaglandins, 1976, 12, 715). The test compound is then pre-incubated with the enzyme for a period of five minutes and its ability to prevent the decrease in tension is subsequently measured.

3. Thromboxane A$_2$ (TxA$_2$) Synthetase

Indomethacin-pretreated human platelet microsomes (Science, 1976, 193, 163) are incubated with PGH$_2$ (produced as described in test No. 1) at 0° C. for a period of two minutes, and aliquots of the reaction mixture are then superfused over two rabbit aorta spirals which are separated by a delay coil (2 min.). The latter is required in order to allow for the selective decay of the more unstable thromboxane A$_2$ (Proc. Nat. Acad. Sci., 1975, 72, 2994), thereby enabling separate measurement of the increased isometric tension due to the TxA$_2$ formed and the PGH$_2$ remaining to take place. The test compound is then pre-incubated with the enzyme for a period of five minutes, and its ability to inhibit the thromboxane synthetase enzyme is measured as its reduction of the TxA$_2$ component of the isometric tension.

Compounds of the invention, when tested in this way, have been shown to be capable of selectively inhibiting the thromboxane synthetase enzyme.

In addition to the above, an in vitro assay test for measuring the inhibition of human blood platelet aggregation has been described and this may be considered predictive of anti-thrombotic efficacy from a clinical point of view (e.g., see Lancet, (ii), 1974, 1223 and J. Exp. Med., 1976, 126, 171). For example, both the clinically-effective agents known as aspirin and sulphinpyrazone, respectively, show inhibitory activity in vitro against a variety of aggregating agents employed in this test.

A number of in vivo tests in animals have also been described for evaluating potential anti-thrombotic drugs. For instance, intravenous injection of arachidonic acid causes death in rabbits by causing platelet clumping and embolization in the lungs. Again, both the clinically-effective aspirin (Agents and Actions, 1977, 1, 481) and sulphinpyrazone (Pharmacology, 1976, 14, 522) protect the rabbit from the lethal effect of the injection. Sulphinpyrazone has also been shown to prevent the aggregation of platelets in an extra corporeal loop of the abdominal aorta of rats in vivo (Thromb. Diathes. Haemostasis, 1973, 30, 138).

Again, the compounds of the present invention are considered to be effective inhibitors of human blood platelet aggregation when subjected to the above in vitro assay, in addition to being useful in protecting rabbits against the lethal effect of arachidonic acid injection and in preventing the aggregation of blood platelets in the rat aorta.

The capsules can be administered orally in the form of tablets or capsules containing a unit dose of the compound together with such excipients as corn starch, calcium carbonate, dicalcium phosphate, alginic acid, lactose, magnesium stearate and talc. The tablets are typically prepared by granulating the ingredients together and compressing the resulting mixture into tablets of the desired size. The capsules are typically prepared by granulating the ingredients together and filling them into hard gelatin capsules of the appropriate size to contain the proper ingredients.

The compounds can also be administered parenterally, for example, by intramuscular, intravenous or subcutaneous injection, or even by infusion of a parenteral solution of same into a vein. For parenteral administration, in general, they are best used in the form of a sterile aqueous solution which may also contain other solutes such as tonic and pH adjusters. The compounds may, e.g., be added to distilled water and the pH subsequently adjusted to a value in the range of pH 3–6 with the aid of an acid such as citric acid, lactic acid or hydrochloric acid, etc. A sufficient amount of other solutes such as dextrose or saline may then be added to the mixture to render the final solution isotonic. The resulting solution is then sterilized according to the method of British Pharmacopoeia, 1973 by filtration through a bacteria-proof filter under aseptic conditions into sterile containers, so as to comply with the test for sterility of Appendix 121 in British Pharmacopoeia, 1973. Suitable containers for these purposes include, for example, sterile glass vials of an appropriate size to contain the desired volume of solution, which volume will typically contain a unit dose of the compound of the formula (I).

For oral administration to human patients, it is expected that the daily dosage level of a compound to be administered will be from about 0.1 to 20 mg/kg. per day for a typical adult patient (70 kg.). For parenteral administration, it is expected that the daily dosage level of a compound of the formula (I) will be from about 0.01–0.5 mg/kg. per day, for a typical adult patient. Thus, tablets or capsules can generally be expected to contain anywhere from approximately 5 to 150 mg of the active compound for administration orally up to three times a day, while dosage units for parenteral administration can be expected to contain roughly from 0.5–35 mg. of the active compound on this basis. A typical vial used in the latter connection would be a 10 ml. vial containing 5 mg. of the active compound made up in 6–10 ml. of sterile solution.

It will, of course, be appreciated that the physician will, in any event, determine the actual dosage to be employed for the present purposes at hand and that this will be the dosage which is most suitable for the individual and it will vary with the age, weight and response of the patient. The above dosages are merely exemplary of the average host. There may, of course, be individual cases where higher or lower dosages are clearly called for, i.e., dosages which are above or below the limits set by the aforementioned ranges.

EXAMPLE 1

A solution consisting of 2-dimethylaminomethyl-3-hydroxypyridine (30.4 g.) and imidazole (13.6 g.) dissolved in xylene (100 ml.) was heated under reflux for a period of five hours and then allowed to cool to room temperature (~25° C.). The resulting precipitated oil was then scratched so as to induce crystallization and the solid product so obtained was thereafter crystallized from isopropanol/petroleum ether (b.p. 60°–80° C.) to afford pure 2-(imidazol-1-ylmethyl)-3-hydroxypyridine (yield, 24.9 g.), m.p. 154°–155° C.

Anal. Calcd. for C$_9$H$_9$N$_3$O: C, 61.88; H, 5.16; N, 23.86. Found: C, 61.70; H, 5.18; N, 23.99.

EXAMPLE 2

A solution consisting of 3-hydroxy-4-methylpyridine (32.7 g.), 30% aqueous dimethylamine (46.5 ml.) and formalin (25 ml.) in water (50 ml.) was heated on a steam bath for a period of two hours. The cooled reaction solution was then extracted with ten-100 ml. portions of diethyl ether and the combined ether and extracts were subsequently dried over anhydrous magnesium sulfate and filtered. After removal of the volatile liquids by means of evaporation under reduced pressure, there was finally obtained an oil as residue which was subsequently distilled in vacuo to give pure 2-dimethylaminomethyl-3-hydroxy-4-methylpyridine (yield, 34.5 g.), b.p. 71°–74° C./0.6 mm. Hg. The corresponding dihydrochloride salt melted at 214°–217° C. (decomp.) after recrystallization from ethanol/diethyl ether.

Anal. Calcd. for $C_9H_{14}N_2O_2.2HCl$: C, 45.20; H, 6.74; N, 11.71. Found: C, 45.26; H, 6.74; N, 11.76.

The procedure described in Example 1 was then repeated except that 2-dimethylaminomethyl-3-hydroxy-4-methylpyridine (4.44 g.) and imidazole (1.82 g.) were reacted in xylene (15 ml.) to afford 2-(imidazol-1-ylmethyl)-3-hydroxy-4-methylpyridine (yield, 3.60 g.), m.p. 170°–172° C. after recrystallization from toluene.

Anal. Calcd. for $C_{10}H_{11}N_3O$: C, 63.47; H, 5.86; N, 22.21. Found: C, 63.71; H, 5.89; N, 22.40.

EXAMPLE 3

The procedure described in Example 1 was repeated except that 2-dimethylaminomethyl-3-hydroxy-6-methylpyridine (16.6 g.) and imidazole (6.8 g.) were reacted in xylene (50 ml.) to afford 2-(imidazol-1-ylmethyl)-3-hydroxy-6-methylpyridine (yield, 14.42 g.), m.p. 153°–155° C. after recrystallization from isopropanol/petroleum ether (b.p. 60°–80° C.).

Anal. Calcd. for $C_{10}H_{11}N_3O$: C, 63.47; H, 5.86; N, 22.21. Found: C, 63.50; H, 5.91; N, 22.18.

EXAMPLE 4

A mixture consisting of 2-chloromethyl-6-methylpyridine hydrochloride (13.35 g.), imidazole (5.10 g.) and sodium carbonate (15.90 g.) in N,N-dimethylformamide (150 ml.) was heated on a steam bath for a period of 18 hours and then evaporated. The residue was taken up in chloroform and the resulting solution was filtered to give a clear filtrate. Evaporation of the latter liquid while under reduced pressure then gave a brown oil, which was subsequently chromatographed on silica gel (150 g.). The column was then eluted with chloroform/methanol (9:1 by volume) and 100 ml. fractions were thereafter collected in the usual manner. The first three fractions were discarded, while the following four fractions were combined and evaporated to dryness while under reduced pressure to give an oil, which was subsequently dissolved in diethyl ether. Treatment of the latter solution with an excess of ethereal hydrogen chloride then gave a crystalline precipitate of the desired hydrochloride salt, which was subsequently recovered by means of suction filtration. Recrystallization of the latter material from ethanol then gave pure 2-imidazol-1-ylmethyl)-6-methylpyridine dihydrochloride (yield, 6.0 g.), m.p. 212°–213° C.

Anal. Calcd. for $C_{10}H_{11}N_3.2HCl$: C, 48.79; H, 5.33; N, 17.07. Found: C, 48.50; H, 5.39; N, 16.92.

EXAMPLE 5

A mixture consisting of 2-chloromethylquinoline hydrochloride (10.0 g.), imidazole (3.2 g.) and sodium carbonate (14.8 g.) in N,N-dimethylformamide (100 ml.) was heated on a steam bath for a period of seven hours and then evaporated. The residue was taken up in chloroform and the resulting solution was filtered to give a clear filtrate. Evaporation of the latter liquid while under reduced pressure then gave a solid substance, which was subsequently crystallized from chloroform/petroleum ether (b.p. 60°–80° C.) and then recrystallized from diethyl ether to give pure 2-(1-imidazol-1-ylmethyl)quinoline (yield, 2.10 g.), m.p. 106°–107° C.

Anal. Calcd. for $C_{13}H_{11}N_3$: C, 74.62; H, 5.30; N, 20.08. Found: C, 74.66; H, 5.14; N, 20.15.

EXAMPLE 6

A solution of 2-(imidazol-1-ylmethyl)-3-hydroxypyridine (3.0 g.) in dry N,N-dimethylformamide (40 ml.) was treated with sodium hydride (0.90 g., 50% suspension in mineral oil) at 0° C., while under a dry nitrogen atmosphere and the resulting suspension was stirred at 0° C. for a period of 30 minutes. Benzyl bromide (2.90 g.) was then added dropwise to the stirred solution and stirring of same was continued for a further hour at 0° C., followed by stirring at room temperature (~25° C.) for a period of two hours. At this point, water (10 ml.) was added to the mixture and the resulting aqueous solution was evaporated to dryness while under reduced pressure. The residue was taken up in chloroform and the inorganic material which remained was subsequently removed by means of filtration. The filtrate so obtained was then concentrated in vacuo and the residue subsequently chromatographed on silica gel. The resulting column was then eluted first with petroleum ether (b.p. 60°–80° C.) to remove the mineral oil and then with chloroform to remove the product. Evaporation of the chloroform solution then gave an oil, which subsequently crystallized on cooling. The latter material was then recrystallized from ethyl acetate/petroleum ether (b.p. 60°–80° C.) to afford pure 2-(imidazol-1-ylmethyl)-3-benzyloxypyridine (yield, 1.5 g.), m.p. 73°–74° C.

Anal. Calcd. for $C_{16}H_{15}N_3O$: C, 72.43; H, 5.70; N, 15.84. Found: C, 72.18; H, 5.67; N, 15.72.

EXAMPLE 7

The procedure described in Example 6 was repeated except that methyl iodide was the alkylating agent of choice employed instead of benzyl bromide, using the same molar proportions as before. In this particular case, the corresponding final product obtained was 2-(imidazol-1-ylmethyl)-3-methoxypyridine, isolated as the fumarate salt, m.p. 175°–176° C. after recrystallization from isopropyl alcohol.

Anal. Calcd. for $C_{10}H_{11}N_3O.C_4H_4O_4$: C, 55.07; H, 4.95; N, 13.77. Found: C, 55.21; H, 5.02; N, 14.04.

EXAMPLE 8

The procedure described in Example 6 was repeated except that 2-(imidazol-1-ylmethyl)-3-hydroxy-6-methylpyridine and methyl iodide were reacted, using the same molar conditions as before. In this particular case, the corresponding final product obtained was 2-(imidazol-1-ylmethyl)-3-methoxy-6-methylpyridine, m.p.69°–70° C. after recrystallization from diethyl ether/petroleum ether (b.p. 60°–80° C.).

Anal. Calcd. for $C_{11}H_{13}N_3O$: C, 65.00; H, 6.45; N, 20.68. Found: C, 65.02; H, 6.72; N, 21.09.

EXAMPLE 9

The procedure described in Example 6 was repeated except that n-propyl bromide was the alkylating agent of choice employed instead of benzyl bromide, using the same molar proportions as before. In this particular case, the corresponding final product obtained was 2-(imidazol-1-ylmethyl)-3-(n-propoxy)pyridine, m.p. 65°–70° C. after recrystallization from diethyl ether/petroleum ether (b.p. 60°–80° C.).

Anal. Calcd. for $C_{12}H_{15}N_3O$: C, 66.34; H, 6.96; N, 19.34. Found: C, 65.93; H, 6.91; N, 1937.

EXAMPLE 10

The procedure described in Example 6 was repeated except that allyl bromide was the alkylating agent of choice employed instead of benzyl bromide, using the same molar proportions as before. In this particular case, the corresponding final product obtained was 2-(imidazol-1-ylmethyl)-3-allyloxypyridine, isolated as the fumarate salt, m.p. 118°–119° C. after recrystallization from isopropanol/petroleum ether (b.p. 60° C.).

Anal. Calcd. for $C_{12}H_{13}N_3O.C_4H_4O_4$: C, 58.00; H, 5.17; N, 12.68. Found: C, 57.95; H, 4.92; N, 12.64.

EXAMPLE 11

The procedure described in Example 6 was repeated except that isobutyl bromide was the alkylating agent of choice employed instead of benzyl bromide, using the same molar proportions as before. In this particular case, the corresponding final product obtained was 2-(imidazol-1-ylmethyl)-3-isobutoxypyridine, isolated as the dihydrochloride monohydrate, m.p. 190°–192° C. after recrystallization from isopropanol/petroleum ether (b.p. 60°–80° C.

Anal. Calcd. for $C_{13}H_{17}N_3O.2HCl.H_2O$: C, 48.45; H, 6.57; N, 14.04. Found: C, 48.18; H, 6.13; N, 13.30.

EXAMPLE 12

The procedure described in Example 6 was repeated except that cyclopropylmethyl bromide was then alkylating agent of choice employed instead of benzyl bromide, using the same molar proportions as before. In this particular case, the corresponding final product obtained was 2-(imidazol-1-ylmethyl)-3-cyclopropylmethoxypyridine, isolated as the oxalate salt, m.p. 152°–154° C. after recrystallization from ethanol.

Anal. Calcd. for $C_{13}H_{15}N_3O.C_2H_2O_4$: C, 56.42; H, 5.37; N, 13.16. Found: C, 56.19; H, 5.33; N, 12.91.

EXAMPLE 13

The procedure described in Example 6 was repeated except that prop-2-ynyl bromide was the alkylating agent of choice employed instead of benzyl bromide, using the same molar proportions as before. In this particular case, the corresponding final product obtained was 2-(imidazol-1-ylmethyl)-3-(prop-2-ynoxy)pyridine, isolated as the dihydrochloride salt, m.p. 147°–149° C. after recrystallization from isopropyl alcohol containing a trace of methanol.

Anal. Calcd. for $C_{12}H_{11}N_3O.2HCl$: C, 50.28; H, 4.65; N, 14.61. Found: C, 50.36; H, 4.58; N, 14.68.

EXAMPLE 14

The procedure described in Example 6 was repeated except that p-methoxybenzyl bromide was the alkylating agent of choice employed instead of benzyl bromide, using the same molar proportions as before. In this particular case, the corresponding final product thus obtained was 2-(imidazol-1-ylmethyl)-3-(p-methoxybenzyloxy)pyridine, isolated as the fumarate salt, m.p. 177°–178° C. after recrystallization from ethanol/petroleum ether (b.p. 60°–80° C.).

Anal. Calcd. for $C_{17}H_{17}N_3O_2.C_4H_4O_4$: C, 61.30; H, 5.15; N, 10.21. Found: C, 61.06; H, 5.15; N, 10.21.

EXAMPLE 15

The procedure described in Example 6 was repeated except that o-methoxybenzyl chloride was the alkylating agent of choice employed instead of benzyl bromide, using the same molar proportions as before. In this particular case, the corresponding final product thus obtained was 2-(imidazol-1-ylmethyl)-3-(o-methoxybenzyloxy)pyridine, isolated as the fumarate salt, m.p. 137°–139° C. after recrystallization from ethanol/diethyl ether.

Anal. Calcd. for $C_{17}H_{17}N_3O_2.C_4H_4O_4$: C, 61.30; H, 5.15; N, 10.21. Found: C, 61.51; H, 5.18; N, 10.49.

EXAMPLE 16

The procedure described in Example 6 was repeated except that p-methylbenzyl bromide was the alkylating agent of choice employed instead of benzyl bromide, using the same molar proportions as before. In this particular case, the corresponding final product thus obtained was 2-(imidazol-1-ylmethyl)-3-(p-methylbenzyloxy)pyridine, m.p. 106°–107° C. after recrystallization from chloroform/petroleum ether, (b.p. 60°–80° C.).

Anal. Calcd. for $C_{17}H_{17}N_3O$: C, 73.09; Hm 6.17; N, 15.04. Found: C, 72.86; H, 6.17; N, 14.97.

EXAMPLE 17

The procedure described in Example 6 was repeated except that p-chlorobenzyl chloride was then alkylating agent of choice employed instead of benzyl bromide, using the same molar proportions as before. In this particular case, the corresponding final product thus obtained was 2-(imidazol-1-ylmethyl)-3-(p-chlorobenzyloxy)pyridine, m.p. 135°–136° C. after recrystallization from chloroform/petroleum ether (b.p. 60°–80° C.).

Anal. Calcd. for $C_{16}H_{14}ClN_3O$: C, 64.11; H, 4.71; N, 14.01. Found: C, 63.73; H, 4.65; N, 13.95.

EXAMPLE 18

A solution consisting of 5-methoxy-2-methylpyridine (12.3 g.) and 30% hydrogen peroxide (12 ml.) dissolved in glacial acetic acid (50 ml) was heated in a steam bath for a period of 12 hours and then allowed to stand overnight (~16 hours) at room temperature (~25° C.). Water (5 ml.) was next added to the mixture, followed by manganese dioxide until effervescence ceased. The resulting mixture was then filtered and the recovered filtrate was subsequently evaporated under reduced pressure to afford crude 5-methoxy-2-methylpyridine-N-oxide (yield, 13.5 g.) as the residual oil.

The crude N-oxide product obtained above (13.5 g.) was then placed in acetic anhydride (100 ml.) and heated on a steam bath for a period of three hours. The excess anhydride was thereafter removed by means of distillation and the liquid residue so obtained was fractionally distilled to give pure 2-acetoxymethyl-5-methoxypyridine (yield, 6.6 g.), b.p. 148°–150° C./12 mm. Hg. This particular product was then hydrolyzed by heating same on a steam bath while in concentrated hydrochloric acid for a period of four hours. Evaporation of the resulting reaction solution then gave crude 2-hydroxymethyl-5-methoxypyridine as the residue.

The crude residue obtained above was then treated with thionyl chloride (50 ml.) and heated under reflux for a period of one hour. The excess thionyl chloride which remained was subsequently removed by means of evaporation under reduced pressure and the solid residue so obtained was thereafter dissolved in water (100 ml.). The resulting aqueous solution was then basified with sodium carbonate, followed by extraction with several fresh portions of diethyl ether. The combined ethereal extracts were next saved and dried over anhydrous sodium sulfate, and subsequently evaporated to near dryness while under reduced pressure to give crude 2-chloromethyl-5-methoxypyridine (yield, 5.0 g.) in the form of a yellow oil which rapidly darkened on standing.

The above oil (5.0 g.) and imidazole (6.5 g.) were then dissolved in dry N,N-dimethylformamide (50 ml.) and the resulting solution was allowed to stand at room temperature (~25° C.) for a period of 18 hours. At the end of this time, the reaction solution was concentrated in vacuo and the resulting residue was subsequently chromatographed on silica gel. Elution of the latter substance with chloroform then gave some initial impurity followed by pure product. The product containing fractions were then collectively combined and subsequently evaporated to near dryness while under reduced pressure, and the resulting residue thereafter dissolved in a small volume of diethyl ether. Treatment of the latter solution with an excess of ethereal hydrogen chloride then gave a crystalline precipitate of the desired hydrochloride salt, which was subsequently recovered by filtration. Recrystallization of the latter material from ethanol/diethyl ether then gave pure 2-(1-imidazol-1-ylmethyl)-5-methoxypyridine dihydrochloride (yield, 3.22 g.), m.p. 204°–206° C.

Anal. Calcd. for $C_{10}H_{11}N_3O \cdot 2HCl$: C, 45.82; H, 5.00; N, 16.03. Found: C, 45.64; H, 5.06; N, 16.22.

EXAMPLE 19

2-(1-Imidazolymethyl)-5-hydroxy-6-chloropyridine

A solution of 2-chloro-3-hydroxypyridine (12.95 g), 50% aqueous dimethylamine (15 ml) and 40% aqueous formaldehyde (10 ml) in water (30 ml) was heated on a steam bath for 2½ hours and then allowed to stand at room temperature (20°) overnight. The solution was evaporated and the residue was taken up in chloroform. The solution was decanted off from some insoluble material, dried ($Na_2SO_4$) and evaporated to small bulk. An excess of ethereal hydrogen chloride was added and the resulting hydrochloride salt was filtered off and crystallised twice from isopropanol to give 2-(dimethylaminomethyl)-5-hydroxy-6-chloropyridine hydrochloride (5.70 g), m.p. 207°–209°.

Analysis %: Found: C, 43.34; H, 5.46; N, 12.85, $C_8H_{11}ClN_2O \cdot HCl$ requires: C, 43.06; H, 5.42; N, 12.56.

This hydrochloride was dissolved in water and the solution was neutralised with dilute sodium hydroxide solution and evaporated. The residue was extracted several times with hot toluene and the combined extracts were filtered and evaporated to give the corresponding free base. The base (3.70 g) and imidazole (1.5 g) were heated under reflux in xylene (50 ml) for 3 hours. The mixture was then evaporated and the resulting dark residue was extracted several times with hot water. The aqueous solution was evaporated and the residue was crystallised first from ethyl acetate and then from water to give 2-(1-imidazolylmethyl)-5-hydroxy-6-chloropyridine (0.88 g), m.p. 157°–158°.

Analysis %: Found: C, 51.52; H, 3.82; N, 20.05; $C_9H_{8}ClN_3O$ requires: C, 51.56; H, 3.85; N, 20.04.

EXAMPLE 20

2-(1-Imidazolymethyl)-5-hydroxypyridine

Boron tribromide (1.0 ml) was added dropwise to a stirred solution of 2-(1-imidazolylmethyl)-5-methoxypyridine (0.0378 g.) (prepared similarly to Example 18 but without converting the end product to the dihydrochloride) in dry methylene chloride (20 ml) at −70° and the resulting mixture was stirred at −70° for 30 minutes, and then at room temperature for 3 hours. Water was then added and the layers were separated. The aqueous layer was made just alkaline with solid sodium bicarbonate and evaporated to dryness. The residue was extracted several times with hot ethyl acetate and the combined extracts were filtered and evaporated until crystallisation commenced. The mixture was allowed to cool and the solid was filtered off to give 2-(1-imidazolylmethyl)-5-hydroxypyridine (0.120 g), m.p. 149°–151°.

Analysis %: Found: C, 61.91; H, 5.22; N, 24.34; $C_9H_9N_3O$ requires: C, 61.70; H, 5.18; N, 23.99.

We claim:

1. A compound of the formula:

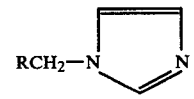

and the pharmaceutically acceptable acid addition salts thereof, wherein R is 2-quinolyl or a pyridyl moiety of the formula:

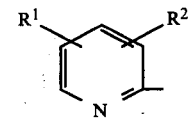

wherein $R^1$ is hydrogen, halogen or alkyl of 1–4 carbon atoms; and $R^2$ is alkyl of 1–4 carbon atoms, or a group of the formula $-OR^3$ wherein $R^3$ is hydrogen, alkyl of 1–4 carbon atoms, allyl, prop-2-ynyl, cycloalkylmethyl having 3–6 carbon atoms in the cycloalkyl group, or benzyl in which the phenyl moiety is unsubstituted on the ring or is monosubstituted with halogen, alkyl of 1–4 carbon atoms or alkoxy of 1–4 carbon atoms; with the proviso that said $-OR^3$ is always a group located at the 3- or 5-positions of the pyridine ring.

2. A compound as claimed in claim 1 wherein R is 2-quinolyl.

3. A compound as claimed in claim 1 wherein R is 2-pyridyl of the formula wherein $R^1$ is hydrogen and $R^2$ is $-OR^3$.

4. A compound as claimed in claim 1 wherein R is 2-pyridyl of the formula wherein $R^1$ is alkyl of 1–4 carbon atoms and $R^2$ is $-OR^3$.

5. A compound as claimed in claim 3 wherein $R^3$ of $-OR^3$ is alkyl of 1–4 carbon atoms.

6. A compound as claimed in claim 3 wherein $R^3$ of $-OR^3$ is unsubstituted benzyl.

7. A compound as claimed in claim 4 wherein $R^3$ of $-OR^3$ is alkyl of 1–4 carbon atoms.

8. 2-(Imidazol-1-ylmethyl)-3-methoxypyridine.

9. 2-(Imidazol-1-ylmethyl)-3-benzyloxypyridine.

10. 2-(Imidazol-1-ylmethyl)-3-methoxy-6-methylpyridine.

11. A pharmaceutical composition suitable for oral or parenteral administration useful for the treatment of ischaemic heart disease, migraine, transent ischaemic attack and stroke, comprising a pharmaceutically acceptable carrier and a therapeutically-effective amount of a compound as claimed in claim 1.

12. The composition according to claim 11 wherein the compound is 2-(imidazol-1-ylmethyl)-3-methoxypyridine.

13. The composition according to claim 11 wherein the compound is 2-(imidazol-1-ylmethyl)-3-benzyloxypyridine.

14. The composition according to claim 11 wherein the compound is 2-(imidazol-1-ylmethyl)-3-methoxy-6-methylpyridine.

* * * * *